(12) United States Patent
Crew et al.

(10) Patent No.: US 12,396,659 B1
(45) Date of Patent: Aug. 26, 2025

(54) HEALTH MONITORING AND LOCATION TRACKING BEHAVIOR MODIFICATION SYSTEM AND ASSOCIATED METHODS

(71) Applicants: Shane Joseph Crew, Pollock Pines, CA (US); Eran Karpen, Haifa (IL); Michael Yudelson, Akrounta (CY)

(72) Inventors: Shane Joseph Crew, Pollock Pines, CA (US); Eran Karpen, Haifa (IL); Michael Yudelson, Akrounta (CY)

( * ) Notice: Subject to any disclaimer, the term of this patent is extended or adjusted under 35 U.S.C. 154(b) by 78 days.

(21) Appl. No.: 18/386,201

(22) Filed: Nov. 1, 2023

Related U.S. Application Data

(60) Provisional application No. 63/421,489, filed on Nov. 1, 2022.

(51) Int. Cl.
*A61B 5/11* (2006.01)
*A61B 5/00* (2006.01)
*H04W 4/029* (2018.01)

(52) U.S. Cl.
CPC ............ *A61B 5/1113* (2013.01); *A61B 5/681* (2013.01); *H04W 4/029* (2018.02)

(58) Field of Classification Search
CPC .................................................... A61B 5/1113
See application file for complete search history.

(56) References Cited

U.S. PATENT DOCUMENTS

| | | | |
|---|---|---|---|
| 2015/0371176 A1* | 12/2015 | Barrett | G06Q 10/0631 705/2 |
| 2016/0335709 A1* | 11/2016 | Salvatore | H04W 4/029 |
| 2018/0047121 A1* | 2/2018 | Bhattacharyya | G16H 15/00 |
| 2018/0197633 A1* | 7/2018 | Mehta | G16H 70/20 |

* cited by examiner

*Primary Examiner* — Travis R Hunnings
(74) *Attorney, Agent, or Firm* — Plager Schack LLP; Mark H. Plager; Stephen Hallberg

(57) ABSTRACT

A health monitoring and location tracking behavior modification system and associated methods are disclosed. The health monitoring and location tracking behavior modification system is configured to monitor health, track location, and modify behavior of a custodial inpatient by way of a wearable wristband device, a beacon device, and a token-based reward system that provides an incentive for positive conduct in the form of digital tokens for entertainment and recreational communication usage of a tablet computing device. The health monitoring and location tracking behavior modification system tracks location and monitors health by a unique wristband device and locator beacons throughout a facility. The pairing of the unique wristband device and locator beacons enable automatic and accurate logging of information about each custodial inpatient in a facility inpatient monitoring log. In this way, the health monitoring and location tracking behavior modification system approaches correctional behavior management proactively and humanely.

9 Claims, 5 Drawing Sheets

HEALTH MONITORING AND LOCATION TRACKING BEHAVIOR MODIFICATION SYSTEM AND ASSOCIATED METHODS

This application claims benefit to U.S. Provisional Patent Application 63/421,489, entitled "A health monitoring and location tracking behavior modification system," filed Nov. 1, 2022. The U.S. Provisional Patent Application 63/421,489 is incorporated herein by reference.

BACKGROUND

Embodiments of the invention described in this specification relate generally to institutional safety systems, and more particularly, to a health monitoring and location tracking behavior modification system and associated methods.

Custodial inpatient persons, institutionalized persons, or other similarly situated persons (hereinafter referred to as "custodial inpatients") are often in situations that trigger negative or damaging behavior. This leads many custodial inpatients to take actions that are not in line with the rules, such as obstructing safety monitoring equipment, engaging in self-harm, harming personnel, defying personnel, etc. Use of safety monitoring equipment is essential for overall safety and compliance with rules since inmate mortality rates (from self-harm or suicide) are significantly higher than mortality rates across society and custodial personnel face a lot of difficulties in managing behavior. Thus, the obstruction of safety monitoring equipment is particularly challenging because when such safety monitoring equipment is used in institutions without obstruction, custodial inpatients can be monitored for safety and custodial personnel working with such custodial inpatients are better prepared to safely engage with them. However, safety monitoring equipment and devices at institutions are chronically obstructed by the custodial inpatients.

Custodial staff and other custodial personnel currently have to dissuade this behavior by confronting the custodial inpatients who obstruct the safety monitoring equipment and possibly even need to punish them, per facility policies or rules. These situations are unpleasant and can lead to verbal or physical altercations, damage, safety concerns, etc. However, current custodial practices struggle to effectively manage inmate behavior. In particular, it can be difficult to enforce disciplinary measures for misbehavior, and the existing practices and systems lack sufficient approaches to incentivize good/positive conduct, instead of merely punishing bad/negative behavior. Yet, a cultural shift in correctional facilities towards reducing use-of-force encounters and minimizing staff litigation risk has created a need for non-violent means of promoting positive inmate behavior.

Adding to this, there are many ongoing challenges when custodial inpatients are released and shortcomings with respect to post-release monitoring of probationers and parolees. While there are some existing post-incarceration systems available, most of these lack key aspects to support successful reintegration into society and fall short in ensuring compliance with release conditions, which can lead to high recidivism rates. A lack of support for health and well-being can also result in probationers and parolees experiencing medical emergencies or fatal overdoses in their communities.

Therefore, what is needed is a way to enhance and ensure safety of, promote positive behavior/conduct by, and streamline communication with institutionalized persons (also referred to as custodial inpatients, custodial inpatient persons, inmates, etc.), and to reduce confrontations between staff and custodial inpatients, while also facilitating rehabilitation within correctional facilities, and provide robust post-release supervision for probationers and parolees which supports their successful reintegration into society.

BRIEF DESCRIPTION

A novel health monitoring and location tracking behavior modification system and associated methods are disclosed. In some embodiments, the health monitoring and location tracking behavior modification system is configured to monitor health, track location, and modify behavior of a custodial inpatient by way of a unique wearable wristband device, a wireless locator beacon device, and a token-based reward system that provides an incentive for positive conduct in the form of digital tokens for entertainment and recreational communication usage of a tablet computing device. In some embodiments, the health monitoring and location tracking behavior modification system is further configured to accurately and automatically log the tracked location and monitored health status of each custodial inpatient in a facility inpatient monitoring log. In this way, the health monitoring and location tracking behavior modification system approaches correctional behavior management proactively and humanely.

In some embodiments, the health monitoring and location tracking behavior modification system comprises (i) a wireless locator beacon device (hereinafter also referred to as the "locator" or the "beacon") for precise location tracking, (ii) a tablet computing device configured for operation by a custodial inpatient for communication, rehabilitation, and entertainment, and (iii) a wearable wristband device (hereinafter also referred to simply as the "wristband") that is worn by the custodial inpatient and is configured to perform realtime health monitoring of the custodial inpatient wearing the wristband, verify identity of the custodial inpatient during operation of the tablet computing device, and track location of the custodial inpatient in realtime via the wireless locator beacon. In some embodiments, the wireless locator beacon is a Bluetooth beacon device or other radio frequency (RF) transmitter. In some embodiments, a plurality of wireless locator beacons are deployed at a plurality of locations where presence of the custodial inpatient is permitted. In this way, the wristband is able to track the location of the custodial inpatient from room to room or in and out of the custodial facility, wherever one of the beacons is deployed.

In some embodiments, the health monitoring and location tracking behavior modification system monitors, in realtime, health and location of an individual wearing the wristband device. In some embodiments, the health monitoring and location tracking behavior modification system provides immediate staff alerts for emergencies related to health or location of the individual wearing the wristband device.

In some embodiments, the health monitoring and location tracking behavior modification system incentivizes positive conduct by way of a token-based reward system that rewards positive conduct of an individual by issuing individual tokens that may be used for communication and interaction with various entertainment or rehabilitative content through the tablet computing device. In this way, the health monitoring and location tracking behavior modification system approaches correctional behavior management proactively and humanely.

In some embodiments, the health monitoring and location tracking behavior modification system further comprises optional safety monitoring equipment that provides visual monitoring and a communication channel to electronically communicate with the custodial inpatient to encourage better behavior or compliance with rules. In this way, the safety monitoring equipment reduces the risk of damage to persons, such as facility staff, or damage to tangible property items. In some embodiments, the safety monitoring equipment comprises a video camera. In some embodiments, the safety monitoring equipment comprises a plurality of video cameras. In some embodiments, the safety monitoring equipment comprises health-data equipment. In some embodiments, the safety monitoring equipment comprises one or more audio devices.

In some embodiments, the methods associated with the health monitoring and location tracking behavior modification system comprise a battery management method and a reward-based behavioral compliance method. In some embodiments, the battery management method ensures sufficient battery charge of electronic devices used in the health monitoring and location tracking behavior modification system. In some embodiments, the reward-based behavioral compliance method encourages positive behavior compliance by a custodial inpatient.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

Figure 1:
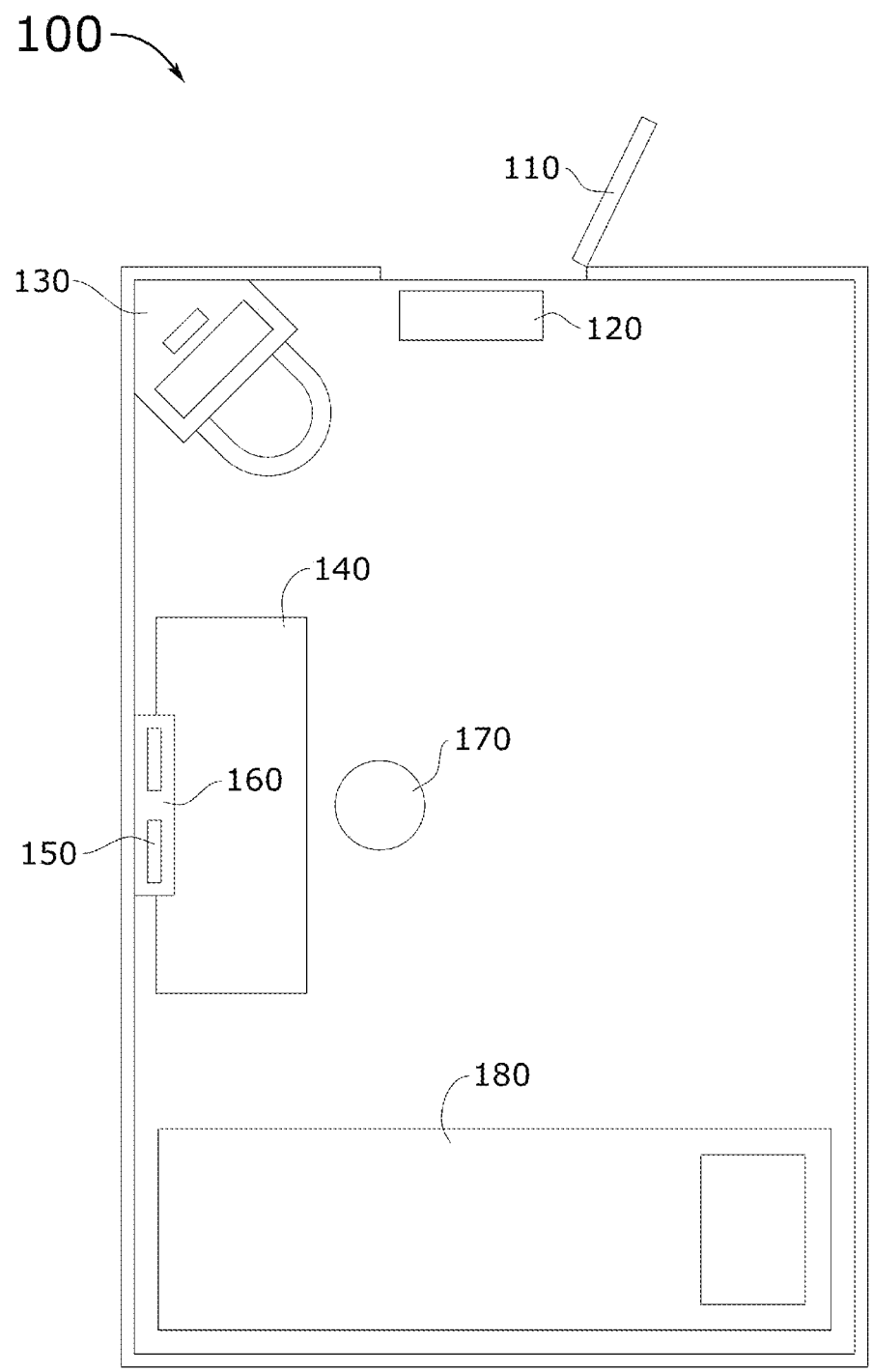
FIG. 1 conceptually illustrates a behavior modification system deployed in a holding cell of a custodial inpatient in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments provide a novel health monitoring and location tracking behavior modification system and associated methods. In some embodiments, the health monitoring and location tracking behavior modification system is configured to monitor health, track location, and modify behavior of a custodial inpatient by way of a unique wearable wristband device, a wireless locator beacon device, and a token-based reward system that provides an incentive for positive conduct in the form of digital tokens for entertainment and recreational communication usage of a tablet computing device. In some embodiments, the health monitoring and location tracking behavior modification system is further configured to accurately and automatically log the tracked location and monitored health status of each custodial inpatient in a facility inpatient monitoring log. In this way, the health monitoring and location tracking behavior modification system approaches correctional behavior management proactively and humanely.

In some embodiments, the health monitoring and location tracking behavior modification system comprises (i) a wireless locator beacon device (hereinafter also referred to as the "locator" or the "beacon") for precise location tracking, (ii) a tablet computing device configured for operation by a custodial inpatient for communication, rehabilitation, and entertainment, and (iii) a wearable wristband device (hereinafter also referred to simply as the "wristband") that is worn by the custodial inpatient and is configured to perform realtime health monitoring of the custodial inpatient wearing the wristband, verify identity of the custodial inpatient during operation of the tablet computing device, and track location of the custodial inpatient in realtime via the wireless locator beacon. In some embodiments, the wireless locator beacon is a Bluetooth beacon device or other RF transmitter. In some embodiments, a plurality of wireless locator beacons are deployed at a plurality of locations where presence of the custodial inpatient is permitted. In this way, the wristband is able to track the location of the custodial inpatient from room to room or in and out of the custodial facility, wherever one of the beacons is deployed.

An example of a deployment of a health monitoring and location tracking behavior modification system is described below, by reference to FIG. 1.

In some embodiments, the wristband continuously monitors the vital signs (heart rate, etc.) of the custodial inpatient and immediately alerts facility staff if any health emergency is detected. This health monitoring feature is specifically designed to prevent suicide attempts and other health crises from escalating unnoticed. By providing the health monitoring feature through the wearable wristband, staff response times are greatly decreased as staff gets alerted as soon as the health crisis arises. In addition to protecting the health of custodial inpatients, the health monitoring feature also significantly reduces inmate mortality at the facility.

As an inmate moves around the facility, or external facility (courthouse, transportation bus, etc.) their location is tracked via wireless beacons (i.e., Bluetooth beacons), ensuring their safety and accountability. This is accomplished via Bluetooth, WiFi, and electronic sim card ("eSim-card") for location tracking and data transfer.

In addition to serving as a health/vital sign monitor, the wristband functions as a unique ID of the custodial inpatient to enable the custodial inpatient to log into the tablet device. Specifically, the wristband device is able to be detected by the tablet when and if the wristband is being worn by the custodial inmate. The tablet provides a controlled digital environment for communication, education, rehabilitative resources, and entertainment. Specifically, each custodial inpatient is assigned a tablet computing device. However, if the custodial patient is not wearing the wristband, it is not possible for the tablet to authenticate the identity of the custodial inpatient. In that case, the tablet prevents any interaction with content by the custodial inpatient. In addition to providing a verifiable unique ID, the wristband device of some embodiments also functions in a continuous monitoring mode. That is, the wristband continues monitoring the area in its proximity and is checked by the tablet for additional security.

In addition to health monitoring and behavioral incentives, another key feature of the health monitoring and location tracking behavior modification system is to streamline the flow of communication within correctional facilities. The wristbands assigned to the custodial inpatients can serve as a digital hub for all notifications. Examples of the types of notifications include, without limitation, timing for recreation periods, lock downs (return to cell), medical calls, visitation schedules, calendar notifications, and any other important announcements. The form of notifications include, without limitation, visual output on a screen (tablet or some versions of the wristband device with a screen), audio output through a speaker of the tablet or wristband device (when a speaker is incorporated into the wristband design), light-based indicators such as lighting up LEDs on the wristband (which is demonstrated and described below, by reference to FIGS. 4 and 5), or other manners of notification.

By providing a centralized, individualized, and real-time platform for conveying such information, the health monitoring and location tracking behavior modification system aims to reduce confusion and potential conflict arising from miscommunication. This streamlined communication feature, while enhancing the operational efficiency of the institution, also empowers the custodial inpatients with better control over their daily routines, thereby fostering a sense of responsibility and self-management.

An example of one type of wearable wristband device utilized in a health monitoring and location tracking behavior modification system is described below, by reference to FIGS. 4 and 5.

A crucial extension of the health monitoring and location tracking behavior modification system is its application to parolees and probationers. A goal of extending the health monitoring and location tracking behavior modification system to applications for parolees and probationers is to provide robust monitoring that assists courts and helps probation and parole officers to ensure compliance with terms of release. When extended in this way, the health monitoring and location tracking behavior modification system can be configured to provide monitoring with respect to adherence to curfews, location-based stay-away orders (such as those ordered in domestic violence situations), participation in mandatory classes (e.g., Alcoholics Anonymous, Narcotics Anonymous, etc.), compliance with court dates and job requirements, and many other aspects. Furthermore, the wristband could be deployed in such external applications of the health monitoring and location tracking behavior modification system and still provide the health monitoring feature, but reconfiguring the alert notification settings to be directed to non-facility emergency medical services (e.g., in case of a medical emergency or an overdose due to a relapse, etc.). Through these features, the health monitoring and location tracking behavior modification system aims to support individuals in their transition back into society, reducing recidivism, and ensuring community safety.

Security is a top priority of the health monitoring and location tracking behavior modification system, particularly for tablet use and communication. While the key security measure requiring the custodial inpatient to be wearing the wristband to allow for his or her identity to be verified, the health monitoring and location tracking behavior modification system provides additional security measures to ensure properly authenticated user identity and otherwise maintain security within the facility. One such security measure is through facial recognition of the custodial inpatient as provided by a facial recognition system of the tablet, In some embodiments, the custodial inpatient must be wearing the wristband to access the tablet to 'sign in'. This first pass security measure then triggers the facial recognition system to capture one or more images or a video of the custodial inpatient to compare to a reference image of the custodial inpatient. In some embodiments, the facial recognition system captures the imagery/video via an onboard camera of the tablet computing device. During the comparison to the reference image, the facial recognition system check one or more unique facial features automatically by way of a computer vision algorithm or an AI-based image recognition algorithm performed by an AI engine (hosted by a server computer at the facility). In some embodiments, the facial recognition system continuously rechecks the visual identity of the person operating the tablet in comparison with the reference image of the custodial inpatient throughout the time during which the tablet is being operated. In this way, the facial recognition system ensures that the custodial inpatient has not handed off the tablet to another user during a call (communication) or while interacting with available educational or entertainment content.

Another security measure provided by the health monitoring and location tracking behavior modification system is a background blurring feature that automatically blurs the background in real-time around and behind the verified custodial inpatient during a video call. The background blurring feature enhances privacy and ensures that the facility's sensitive areas are not visible to external viewers. The transmission mechanism for video and/or audio calls (and optionally for overall data communications) may be WiFi, cellular connectivity to a communication tower ("cell tower"), or other wireless communication mechanisms.

The health monitoring and location tracking behavior modification system also provides a call recording and transcription method as a security feature. Specifically, the call recording captures all audio for audio-only communication and captures video (both audio and visual) of video calls. The recorded calls are saved to a facility database storage that is communicably connected to a facility server computer, accessible to every tablet via WiFi. Furthermore, a transcription software application is installed on the facility server computer and is configured to automatically transcribe each recorded call for future reference, analysis, security, and legal reasons. In some embodiments, the wristband supports a voice recognition feature in which all conversations in proximity of a wristband (worn by any custodial inpatient or even staff) may be voice recognized, recorded, and analyzed by the AI engine for content. For security, inappropriate content may trigger the alert notification system of the health monitoring and location tracking behavior modification system to send an alert notification to an operator or staff for relevance.

Another security measure provided by the health monitoring and location tracking behavior modification system is an external user verification system. This security feature is provided to ensure that the user at the other end of a communication utilizes a dedicated application on their mobile device (e.g., iphone, Android device, etc.) or a dedicated web app when operating a traditional computer or laptop a connected through a web browser or web platform. Their identity is also verified before any communication takes place.

In some embodiments, the health monitoring and location tracking behavior modification system further comprises optional safety monitoring equipment that provides visual monitoring and a communication channel to electronically communicate with the custodial inpatient to encourage better behavior or compliance with rules. In this way, the safety monitoring equipment reduces the risk of damage to persons, such as facility staff, or damage to tangible property items. In some embodiments, the safety monitoring equipment comprises a video camera. In some embodiments, the safety monitoring equipment comprises a plurality of video cameras. In some embodiments, the safety monitoring equipment comprises health-data equipment. In some embodiments, the safety monitoring equipment comprises one or more audio devices. The communication channel transmission mechanism may be WiFi, cellular, or other wireless communication mechanisms.

In some embodiments, the methods associated with the health monitoring and location tracking behavior modification system comprise a battery management method and a reward-based behavioral compliance method. In some embodiments, the battery management method ensures sufficient battery charge of electronic devices used in the health monitoring and location tracking behavior modification system. A description of a battery management method is described below, by reference to FIG. 2. In some embodiments, the reward-based behavioral compliance method encourages positive behavior compliance by a custodial inpatient. A description of a reward-based behavioral compliance method that encourages positive behavior compliance by a custodial inpatient is described below, by reference to FIG. 3.

Embodiments of the health monitoring and location tracking behavior modification system described in this specification address the problems noted above by providing custodial inpatients with computerized devices for communication, education, and entertainment as a reward for compliant (non-obstructing) behavior, and, when a custodial inpatient obstructs safety monitoring equipment, automatically stopping the operable functions of the computerized devices used by the custodial inpatient causing the obstruction. In some embodiments, the computerized devices will automatically stop working for a period of time. In some embodiments, the computerized devices will not resume functional operation until the obstruction is removed. In some embodiments, the computerized behavioral compliance method further rewards compliant custodial inpatients who do not obstruct the safety monitoring equipment for a designated period of time by additional rewards that include credits towards voice calls, entertainment, and other desired objects or opportunities, etc.

The health monitoring and location tracking behavior modification system of the present disclosure generally works by a positive reinforcement mechanism that encourages custodial inpatients to behave in acceptable ways. The wristband device is a key aspect of the system, but optional safety monitoring equipment can be deployed as well. The safety monitoring equipment may include any of a variety of devices including, without limitation, video cameras (see movement), infrared sensors (oxygen saturation, heart-rate), FLIR cameras (thermal imaging), audio sensors (respiration), etc.

As noted above, many institutions allow custodial inpatients to use devices, such as tablet computing devices or computers, in the custodial facility (e.g., jail, prison, psych-hospital, etc.). Voice calls, movies, music, and other entertainment are often subscription based, generally paid for by the custodial inpatient or their loved ones who place credits on their account for usage. As such entertainment is valued by most custodial inpatients, it is likely to impact behavior of custodial inpatients who realize they can earn additional credits with compliant (non-obstructing) behavior. Also, the purpose of making the safety monitoring equipment electronically communicate with the tablets (used by such custodial inpatients) is to encourage the custodial inpatient from obstructing safety monitoring equipment. The health monitoring and location tracking behavior modification system described in this specification accomplishes these goals by limiting use of the tablets when safety monitoring equipment is obstructed or tampered with and rewarding custodial inpatients with credits when compliance is actualized over a span of time. Thus, when any given custodial inpatient behaved well during the time period, they will be given credits (tokens) towards usage of their tablet for voice calls, movies, music, etc.

Overall, the health monitoring and location tracking behavior modification system of the present disclosure increases the safety of inmates and other custodial inpatients, reduces confrontations of staff addressing behavior problems by encouraging desired behavior of custodial inpatients with the provided tablets, and provides a more manageable and safer institution for all.

An example of how the health monitoring and location tracking behavior modification system of the present disclosure can be utilized in practice, imagine the health monitoring and location tracking behavior modification system being deployed at a facility where each custodial inpatient is assigned and provided a wristband device to wear, two external batteries to maintain expected charging levels, and a tablet computing device which is accessible for entertainment, communication and other education resources when the custodial inpatient behaves according to expectations. Further imagine that the tracking of health and location is automatic, and a notification system provides immediate alerts when the wristband is removed or not fully charged or other infractions. This is a key reason for providing each custodial inpatient with two 'external' batteries that are, in essence, swappable. In other words, when one of the external batteries is installed in the wristband device, the other external battery should be charging. When the external battery in the wristband reaches the threshold level of reduced charge, the custodial inpatient would only need to take out the external battery from the wristband and replace it with the fully charged (other) external battery. In this way, none of the custodial inpatients ever have to remove the wristband from their wrist in order to charge the device. As such, the wristband provides the constant monitoring as needed by the facility. In addition to automated notifications, imagine the system has a reward allocation system to proactively encourage compliance and improve behavior by the custodial inpatients. This is all done by combining the tablet usage with the wristband device, along with location tracking via wireless beacon devices, and health monitoring sensors/devices integrated into the wristband device, thereby enabling the system to continuously capture and monitor health data and vital signs of the custodial inpatients, as well as their location.

By way of example, FIG. 1 conceptually illustrates a health monitoring and location tracking behavior modification system deployed in a holding cell 100 of a custodial inpatient. As shown in this figure, the health monitoring and location tracking behavior modification system deployed in the holding cell 100 of the custodial inpatient includes a cell door 110, safety monitoring equipment 120, a toilet/sink 130, a desk 140, a tablet computing device 150 assigned to the custodial inpatient, a wall-mounted battery charging station 160, a stool 170, a bed 180, and a wireless locator beacon device 190.

The cell door 110, the toilet/sink 130, the desk 140, the stool 170, and the bed 180 are common items that are part of or found in a holding cell of a custodial patient. The health monitoring and location tracking behavior modification system of the present disclosure contributes additional items not normally part of or found in a hold cell. The extra items shown in this figure are the safety monitoring equipment 120, the tablet computing device 150 assigned to the custodial inpatient, the wall-mounted charging station 160, and the wireless locator beacon device 190. In addition to these items, the custodial patient is given a wireless wristband device to wear and two external batteries-one for placement alongside the internal, fixed battery of the wireless wristband device, and another to charge at the wall-mounted battery charging station 160 (or store when fully charged).

When the external battery used in the wireless wristband device reaches a threshold charge level, the custodial inpatient swaps out the battery in the wireless wristband device and replaces it with the other external battery, which is fully charged. In some embodiments, the threshold charge level is fifty percent. Accordingly, when the amount of available charge in the external battery used in the wireless wristband device falls below fifty percent, a notification is automatically sent to the tablet computing device 150 and the wireless wristband device itself. The notification triggers the wireless wristband device to provide a visual cue (such as lighting up a particular light in a particular color) as a reminder to switch the battery with the fully charged external battery. The notification sent to the tablet computing device 150 triggers the tablet to output a message instructing the custodial inpatient to replace the depleting external battery in the wireless wristband device with the fully charged external battery and to recharge the insufficiently charged external battery at the wall-mounted battery charging station 160. In this way, the custodial inpatient is responsible for maintaining sufficient battery charge as required. Similarly, the custodial inpatient is responsible for charging the tablet computing device 150 when not in use. The tablet computing device 150 is also charged at the wall-mounted battery charging station 160. When the custodial inpatient fails to responsibly maintain charge levels of the external batteries and/or the tablet computing device 150, there are consequences to the custodial inpatient, as described below, by reference to FIGS. 2.

One of the key extra items shown in this figure is the wireless locator beacon device 190. The wireless locator beacon device 190 of some embodiments is a Bluetooth wireless locator beacon device 190 that pairs with the wireless wristband device worn by the custodial inpatient. In this way, the location of the custodial inpatient is detected and automatically logged. When logging the detection of the custodial inpatient's wireless wristband device, certain information is accurately recorded in a log file, such as in a facility inpatient monitoring log associated with each custodial inpatient. The information includes at least the location (e.g., in the hold cell), a time of detection, and the identity of the custodial inpatient, obtained via a unique ID of the wireless wristband device assigned to the custodial inpatient, time in the holding cell, recreation time, health metrics data, etc.

As noted above, the safety monitoring equipment 120 is optional equipment. However, when deployed with other components of the health monitoring and location tracking behavior modification system, the safety monitoring equipment may enhance security or provide additional safety benefits. Examples of the optional safety monitoring equipment 120 include components which provide visual monitoring and/or communication for staff to see within the holding cell and to electronically communicate with the custodial inpatient to encourage better behavior or compliance with rules. For example, the safety monitoring equipment 120 may include a video camera or multiple video cameras, along with an audio communication channel (either one-way or two-way depending on deployment). Furthermore, the safety monitoring equipment 120 may include other devices or health-data equipment.

In some embodiments, the wearable wristband device (or "wristband") houses two batteries. In some embodiments, the two batteries comprise an internal, non-removable battery and an external, swappable battery. In some embodiments, each inmate is provided with two external, swappable batteries. One of the external, swappable batteries resides within the wristband, while the other external, swappable battery charges in the tablet by way of the tablet's onboard battery. As noted above, the external batteries provide enough power/charge resources so that none of the custodial inpatients ever need to take off the wristband device. This is a crucial way to ensure that monitoring via the wristband is as comprehensive and complete as required by the facility. So, when one of the external batteries is installed in the wristband device, it is simply providing operational power to the wristband. At the same time, the other external battery should be charging (if not, the notifications should be sent to prompt for charging). Since each custodial inpatient is responsible for managing the usage of the external batteries (in terms of their power usage in the wristband and their charging usage at the charging station), the two external batteries work as an effective mechanism to ensure compliance. Then, when the external battery management is handled properly by the custodial inpatient, the wristband will be able to provide the constant monitoring as needed by the facility.

In some embodiments, the tablet computing device (or "tablet") is configured for inmate use for communication, rehabilitation, or entertainment. In some embodiments, functionality of tablet is contingent on both batteries being in place and the wristband battery having at least 50% charge. When the wristband's external battery drops below 50%, a notification is sent to the tablet and the wristband, indicating that the batteries need to be switched out to maintain normal tablet operations. If the battery level drops to 10%, a notification is sent to the staff to ensure compliance and avoid power loss. To promote good practice in battery management and ensure uninterrupted service, the health monitoring and location tracking behavior modification system incorporates a unique feature: when the tablet is not in use and not on the charger, it will emit a chirp sound every five minutes and send a notification to the user's wristband, instructing the inmate to place the unused tablet back onto the wireless charger located in their cell.

Details of how the health monitoring and location tracking behavior modification system encourages proactive battery management by the custodial inpatients are demonstrated by way of a wristband device battery charge management method that is described next, by reference to FIG. 2.

Figure 2:
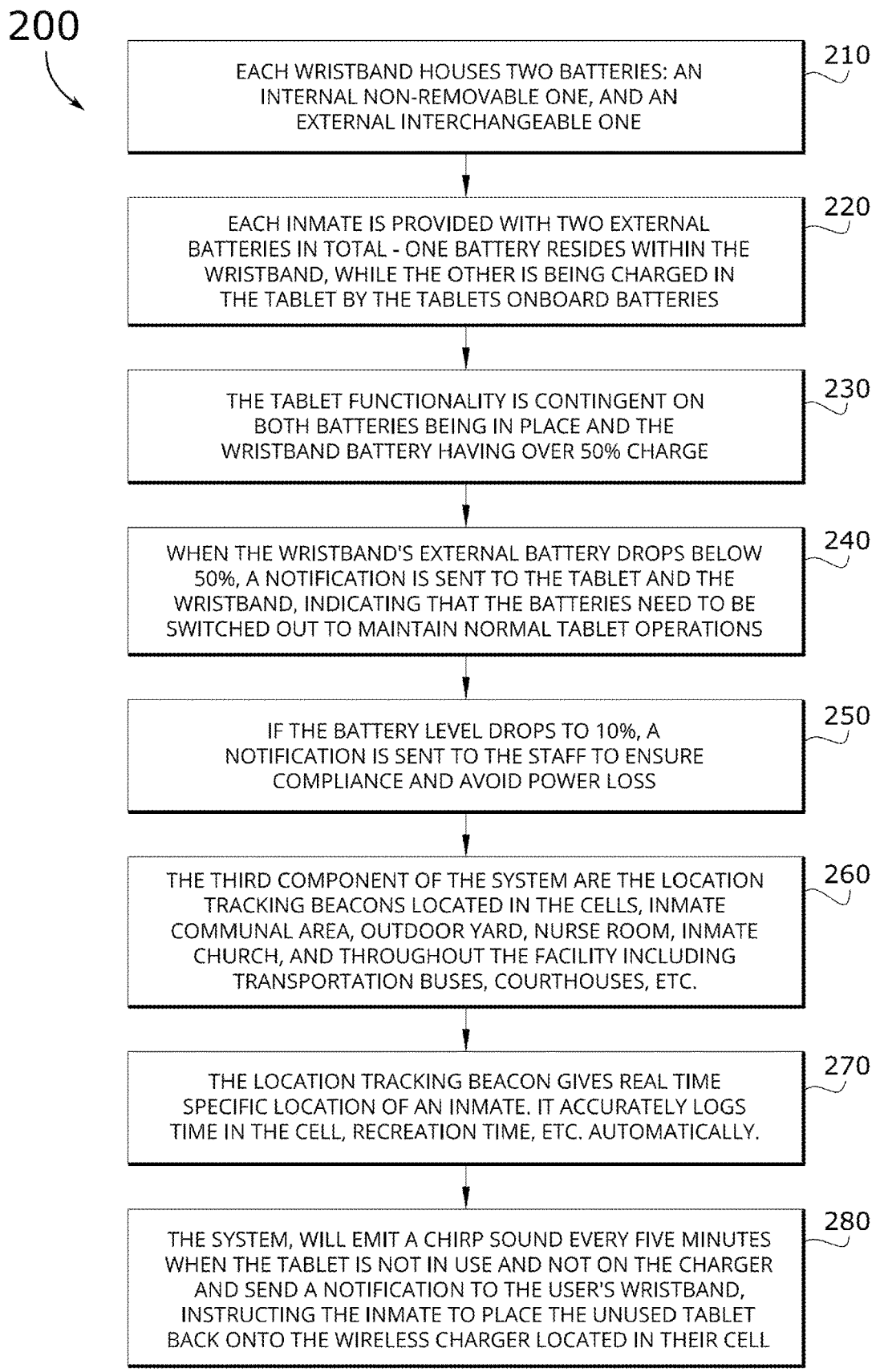
FIG. 2 conceptually illustrates a wristband device battery charge management method in some embodiments.

Specifically, FIG. 2 conceptually illustrates a wristband device battery charge management method 200. As shown in this figure, the wristband device battery charge management method 200 works in connection with a wristband device (for each custodial inpatient) that houses two batteries—an internal, non-removable battery and an external, interchangeable battery (at 210). Other deployments of the health monitoring and location tracking behavior modification system or re-deployments of the health monitoring and location tracking behavior modification system could involve upgraded wristband devices in which more than one external battery is used in the wristband, or some other configuration for the wristband and battery allocation standard implemented at a particular facility.

Also, the wristband device battery charge management method 200 is related to a particular deployment of the health monitoring and location tracking behavior modification system in which there is a wristband and battery allocation standard in which each custodial inpatient is allocated with two external batteries in total (at 220). One of the external batteries is placed in the wristband device and the other external battery allocated to the custodial inpatient connected to the wall-mounted battery charging station 160 or connected to the tablet computing device to charge via the tablet's onboard batteries (at 220).

The wristband device battery charge management method 200 constrains the functionality of the tablet computing device by making the tablet functionality contingent on both batteries being in place—one of the external batteries placed in the wristband device for power consumption by the wristband, while the other external battery allocated to the custodial inpatient is charging—and requiring the external battery in the wristband device to have at least an available remaining charge level of fifty percent (at 230).

If and when the charge level of the external battery in the wristband device dips lower than fifty percent, the wristband device battery charge management method 200 of some embodiments sends a notification to the tablet and to the wristband (at 240). Specifically, the notification indicates that normal tablet functionality cannot be maintained unless the external battery in the wristband device is charged. The notification indicates that the external battery with insufficient charge level (below fifty percent) should be switched out and replaced by the charging external battery (which should be fully charged or at least charged to a level over fifty percent charge). After switching out the external battery with insufficient charge level, the custodial inpatient would recharge it by connection to the tablet computing device (for charging by onboard batteries) or by charging at the wall-mounted charging station 160 in the hold cell of the custodial inpatient.

If and when the charge level of the external battery in the wristband device drops to ten percent remaining charge level, the wristband device battery charge management method 200 sends a notification to facility staff to ensure compliance with battery charge expectations and to avoid power loss by the wristband device (at 250). This would occur if the custodial inpatient wearing the wristband device ignores the first notification (at 240). For instance, the custodial inpatient fails to recharge the external battery with the insufficient charge level (below fifty percent) even after normal tablet operations have ceased.

This is a problem since the wristband device is a key component in health monitoring, location tracking, and verification of identity for logging such data. Thus, maintaining sufficient charge is a crucial aspect for maintaining a system to encourage good, positive behavior of custodial inpatients. While the wristband device is a central component for location tracking, another device is also central to the functionality of location tracking. This would be the locator beacons, such as Bluetooth locator beacons. The wristband device battery charge management method 200 covers placement of several locator beacons throughout the facility (at 260) including one locator beacon in each holding cell for each custodial inpatient and one or more locator beacons in each of several other areas in and around the facility. For instance, locator beacons may be placed in communal areas, outdoor yard areas of the facility, nurse/medial rooms, a place of religious worship located in the facility, and other areas connected to the facility, such as transportation buses, courthouses, etc.

By pairing each custodial inpatient's wristband to a locator beacon, the wristband device battery charge management method 200 is able to accurately track location of the custodial inpatients in realtime (at 270). Furthermore, the location of each custodial inpatient and time of detection is automatically logged, in a facility inpatient monitoring log for each custodial inpatient as determined by the associated unique ID of the wristband device worn by the custodial inpatient. In addition to accurate logging of the custodial inpatient's location, the logging feature also automatically logs other data points, such as time data (e.g., time in holding cell, recreation time, etc.) and health metrics data (e.g., heart rate data, temperature, etc.), among other automatically and accurately logged information about each custodial inpatient.

In another aspect, the wristband device battery charge management method 200 enacts an additional battery management notification mechanism by way of emitting a chirp sound at timed intervals (e.g., every five minutes) for as long as needed when the tablet is not in use and is not connected to the wall-mounted charging station 160 or otherwise being charged (at 280). In addition to emitting the chirping sound at the timed intervals, the wristband device battery charge management method 200 sends notification to the wristband device of the custodial inpatient assigned to the tablet (at 280). The notification sent to the wristband device is typically in the form of a visual cue, such as flashing a red light through one or more of the LED lights of the wristband device. The visual cue represents an instruction for the custodial inpatient to place the unused tablet computing device back at the wall-mounted charging station 160 in their holding cell, or otherwise connect to a charging unit, such as a wireless charger that may be present in communal area. In this way, the wristband device battery charge management method 200 encourages custodial inpatients to proactively and responsibly ensure compliance with battery charge level expectations of the facility, or when failing to do so, to remind the custodial inpatients via notifications and possible ramifications that result in loss of or reduced usage of tablet features, etc.

Beyond encouraging battery management by the custodial inpatients, the health monitoring and location tracking behavior modification system is also designed to encourage positive behavior of custodial inpatients. When custodial inpatients demonstrate good, positive behavior, the full range of tablet functionalities will be rewarded to them in the form of tokens which are redeemable toward usage of the tablet computing device for its entertainment, communication, and other features. Furthermore, the custodial inpatients can purchase personal items with the tokens, which again are rewarded for demonstrating and practicing good, positive behavior. Good, positive behavior is determined on a facility-by-facility basis. However, general conduct considered to be good, positive behavior includes proper usage of the tablet and the wristband, adherence to facility rules, following lockdown rules instructions for orderly returning to their cell, avoiding physical altercations or fights, avoiding verbal altercations, maintaining cell cleanliness, maintaining a respectful demeanor throughout the day, etc. Each day at lockdown, custodial inpatients who have demonstrated good, positive behavior are given a standard allotment of tokens to reward them for the good behavior. The standard allotment of tokens is a sufficient amount of tokens to pay for functionality of the tablet on another day (typically intended for tomorrow's tablet usage). When custodial inpatients demonstrate good, positive behavior for a week, those custodial inpatients are rewarded with extra tokens that they can use at the inmate store for purchases of various items (e.g., to purchase soda, candy, beef jerky, etc.). The deployment configuration of the health monitoring and location tracking behavior modification system can be customized to meet each particular facility's needs.

In cases of disciplinary action, the tablet functionalities and features can be reduced or removed for a duration of time determined by facility staff. For instance, if an inmate fights he or she will lose entertainment and recreational communication functionality and may lose tokens for the inmate store. However, health applications and access to legal and medical communication will remain available irrespective of behavior. In some embodiments, a constant communication channel is provided to each tablet computing device to ensure that each custodial inpatient has access to legal and medical communication at any time. In some embodiments, the constant communication channel is through a WiFi band that is separate from another WiFi band used for other optional entertainment and recreational communication usage of the tablet. In some embodiments, the constant communication channel is provided via cellular connectivity that is configured to only allow the communication for legal and medial communication, while allowing other entertainment and recreational communication happen over a common WiFi channel (or WiFi band).

Details of how the health monitoring and location tracking behavior modification system encourages good, positive behavior and conduct by custodial inpatients are demonstrated by way of a reward-based behavioral compliance method for encouraging positive behavior compliance by a custodial inpatient, described next by reference to FIG. 3.

Figure 3:
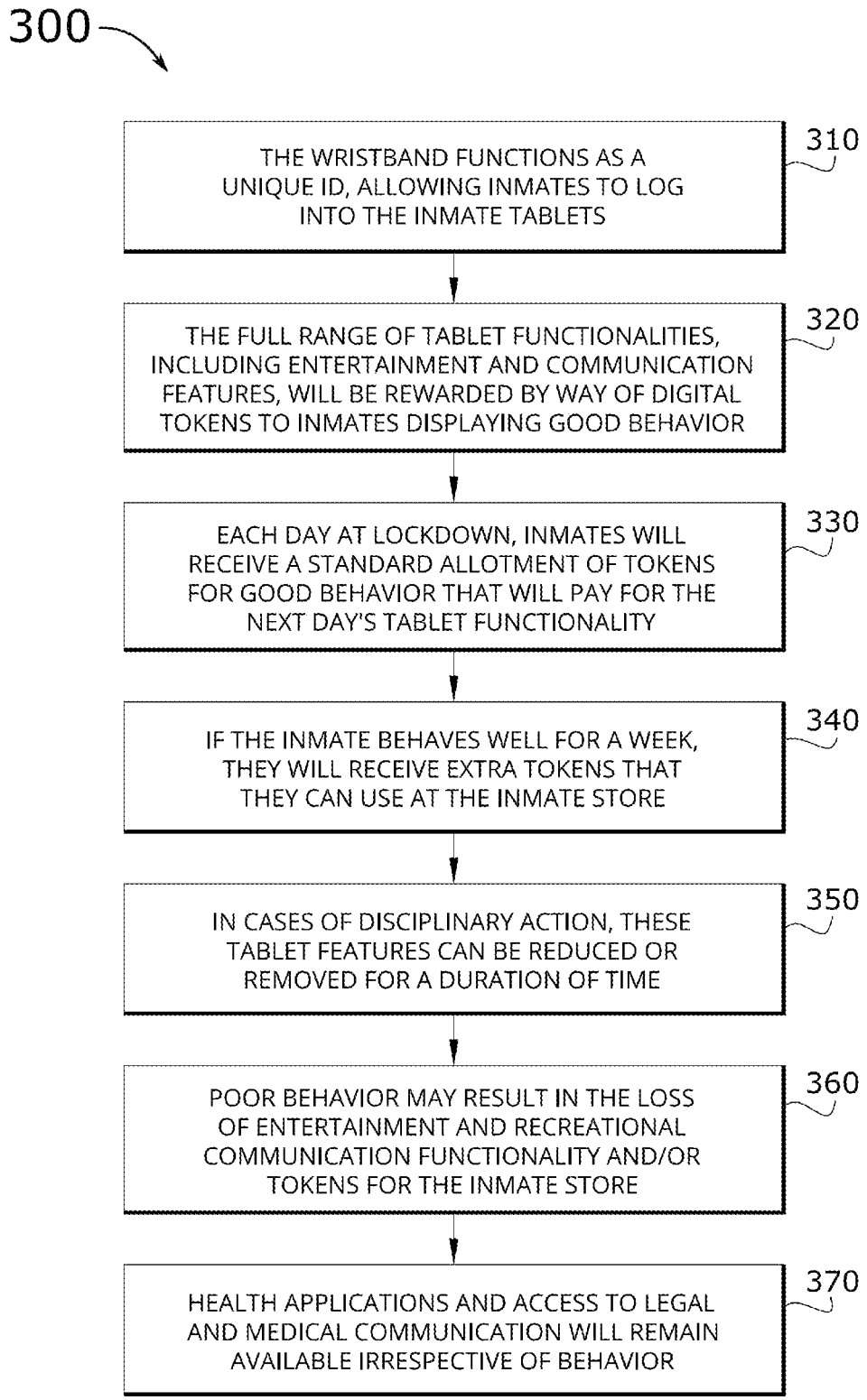
FIG. 3 conceptually illustrates a reward-based behavioral compliance method for encouraging positive behavior compliance by a custodial inpatient in some embodiments.

Specifically, FIG. 3 conceptually illustrates a reward-based behavioral compliance method 300 for encouraging positive behavior compliance by a custodial inpatient. As shown in this figure, the reward-based behavioral compliance method 300 is related to a facility's deployment of the health monitoring and location tracking behavior modification system in which there is a tablet allocation and wristband-based identity verification standard in which each custodial inpatient is allocated one tablet computing device and one wristband device the is uniquely identified as being allocated to a custodial inpatient. In this way, the wristband device functions as a unique ID to verify identity of the custodial inpatient for a range of functions including at least (i) the ability to log on and access content on the tablet assigned to the custodial inpatient, (ii) monitoring health and vital signs of the custodial inpatient, and (iii) tracking location of the custodial inpatient by pairing the wristband device to a locator beacon present in any of several areas in and around the facility. Therefore, in terms of encouraging good, positive behavior and conduct in connection with the reward-based behavioral compliance method 300, the wristband device functions as a unique ID for each custodial inpatient and, assuming the custodial inpatients are wearing their wristbands and have practiced proper battery management, the wristband's unique ID enables those custodial inpatients to log into and access content on their tablets (at 310).

Notably, the full range of tablet functionalities, including entertainment and recreational communication features, are accessible to custodial inpatients by way of digital tokens. However, the digital tokens are not freely available to custodial inpatients. Instead, the token-based reward system is utilized to distribute digital tokens to custodial inpatients who demonstrate good, positive behavior and avoid negative behavior or conduct. In this way, the reward-based behavioral compliance method 300 provides an incentive for good, positive behavior and conduct in the form of digital tokens being rewarded for their demonstrated good, positive behavior and conduct (at 320).

The incentive for demonstrated good behavior is actualized each day at lockdown (or each day at some other time as determined by the facility). Specifically, the custodial inpatients who have demonstrated good, positive behavior throughout the day receive a standard allotment of tokens. In some embodiments, the standard allotment of tokens is a number of digital tokens sufficient to pay for access to the entertainment and recreational communication features of the tablet computing device. The access to the entertainment and recreational communication features is typically accessed on the following day, since digital token distribution for good behavior is normally done at lockdown of the current day. However, in some embodiments, a custodial inpatient can save digital tokens for later days or for other uses, such as at the facility store. The way this works depends on the configuration settings of the token-based reward system for each particular health monitoring and location tracking behavior modification system deployment. Thus, in some embodiments, the standard allotment of tokens is only available to access the entertainment and recreational communication features of the tablet during the next day. After lockdown the next day, any remaining tokens from the standard allotment of tokens rewarded at the prior day's lockdown are deleted, meaning they effectively evaporate if not used during the next day. In some embodiments, this is determined by configuration settings that specify evaporation rules. Thus, the evaporation rules at one facility may differ from another facility. Accordingly, in some other embodiments, unused tokens from the standard allotment of tokens do not evaporate at the next day's lockdown. Instead, unused tokens are automatically saved to a digital storage or digital wallet associated exclusively with the custodial inpatient. Furthermore, in these embodiments, the custodial inpatient may proactively elect to save some or all of the standard allotment of tokens for later use (storing them in the digital storage or wallet).

Additionally, the distribution of the digital tokens itself may vary according to the particular settings of the health monitoring and location tracking behavior modification system as deployed by any given facility. In some embodiments, the token-based reward system is configured to automatically distribute the standard allotment of tokens to the tablet computing devices of those custodial inpatients who have been rewarded for their behavior on the given day. This applies whether the standard allotment of tokens are subject to evaporation rules at the facility or the facility allows custodial inpatients the choice of saving tokens, spending tokens on tablet features, or spending token on tangible items from the facility store.

In some embodiments which allow custodial inpatients the choice of how to use the standard allotment of tokens (i.e., those deployments in which the standard allotment of tokens are not subject to evaporation rules), the standard allotment of tokens (rewarded at lockdown) are provided through a scannable QR code that enables each custodial inpatient to choose a destination for the digital tokens. The destinations available include the tablet computing device (for usage, typically, for the next day's tablet recreational communication and/or entertainment features), a digital storage or digital wallet exclusively associated with the custodial inpatient (for long-term saving of tokens, typically to use in connection with purchases of tangible items from the facility's store), or the facility's store for purchase of one or more items. When the QR code is scanned, a notification on the tablet computing device (or at a device of the facility store) prompts the custodial inpatient to choose and confirm a destination and specify a number of tokens to commit to the destination. This deducts from the remaining balance of digital tokens rewarded for the day (if any remain). In this way, the reward-based behavioral compliance method 300 reinforces the good, positive behavior and conduct of custodial inpatients by rewarding their good behavior demonstrated during the current day with digital tokens to pay for access to the next day's tablet entertainment and recreational communication features (at 330).

In addition to the standard allotment of digital tokens for good behavior demonstrated by custodial inpatients throughout the day, the health monitoring and location tracking behavior modification system may reward custodial inpatients with extra tokens (beyond the standard daily allotment) when they have demonstrated good behavior for an extended period of time, such as a week. In this way, the reward-based behavioral compliance method 300 ensures that custodial inpatients who demonstrated daily good behavior each day of the time period (e.g., one week) are rewarded with the standard allotment of tokens each day and also rewarded with extra tokens (at 340) which can be used at the facility store to purchase tangible items, or can be saved for later use (in the digital storage/wallet associated with the custodial inpatient).

The steps described above (at 310-340) for the reward-based behavioral compliance method 300 are associated with the token-based reward system of the health monitoring and location tracking behavior modification system. In addition to encouraging good, positive behavior and conduct, the reward-based behavioral compliance method 300 also discourages bad, negative behavior and conduct, and does so through disciplinary settings of the token-based reward system of the health monitoring and location tracking behavior modification system. For instance, in cases of disciplinary action for bad, negative behavior or conduct, the reward-based behavioral compliance method 300 reduces or removes the entertainment and recreational communication features of the tablet computing device (at 350), regardless of any aggregation of digital tokens the badly behaving custodial inpatient may have saved in their token storage/wallet. This is a discouragement in two ways—first, the badly behaving custodial inpatient does not receive the standard allotment of digital tokens at lockdown, but their next day (or next days') access to the entertainment and recreational communication features of the tablet is reduced or removed, even if the custodial inpatient has saved tokens to spare.

Furthermore, the reward-based behavioral compliance method 300 of some embodiments also reduces or removes tokens saved for use at the facility store or for future use of the entertainment and recreational communication features of the tablet (at 360). Thus, instead of merely reducing or removing tablet features (at 350), the reward-based behavioral compliance method 300 of some embodiments reduces/removes actual saved tokens of badly behaving custodial inpatients as a form of deterrent against bad, negative behavior or conduct. However, the reward-based behavioral compliance method 300 ensures that some tablet features always remain accessible to every custodial inpatient, whether behaving positively or behaving negatively. Those features include at least health applications, access to legal communication features, and access to medical communication features. Thus, the reward-based behavioral compliance method 300 ensures that legal and medical communication features, as well as health applications, remain available on the tablet and accessible to the custodial inpatient associated with the tablet, irrespective of behavior or disciplinary action (at 370).

In addition to the tablet computing device, a central feature of the health monitoring and location tracking behavior modification system is the wireless wristband device. An example design of one such wireless wristband device is described next, by reference to FIGS. 4 and 5.

Figure 4:
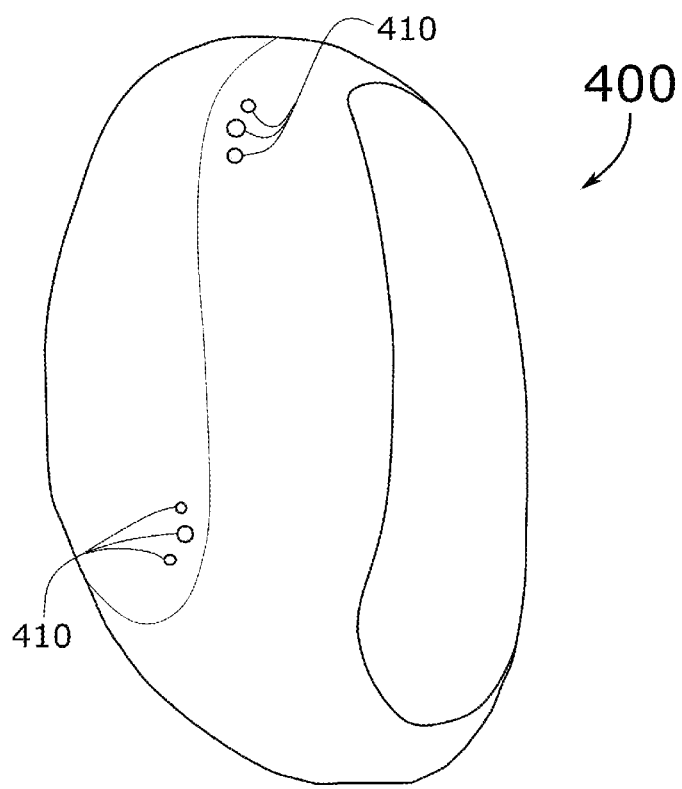
FIG. 4 conceptually illustrates a top side perspective view of a wireless wristband device in some embodiments.
Figure 5:
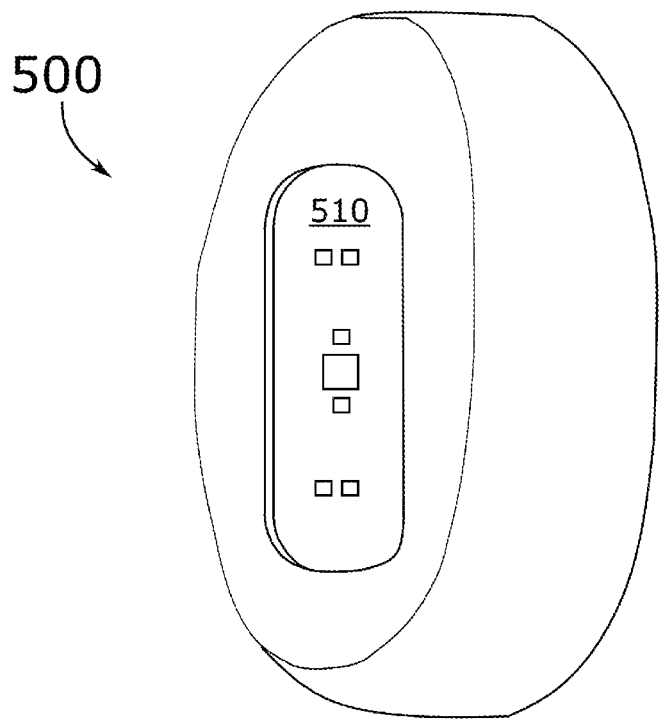
FIG. 5 conceptually illustrates a bottom side perspective view of the wireless wristband device in some embodiments.

By way of example, FIGS. 4-5 conceptually illustrate a wireless wristband device utilized in a health monitoring and location tracking behavior modification system. Specifically, FIG. 4 illustrates a top side perspective view of an exemplary wireless wristband device 400, while FIG. 5 illustrates a bottom side perspective view of the exemplary wireless wristband device 500. As shown in FIG. 4, the top side of the wireless wristband device 400 demonstrates alert lights 410 which illuminate in ways to inform the inmate when the battery needs to be charged. As noted above, the wristband houses two batteries—an internal, non-removable battery and an external, swappable battery. Each inmate is provided with two external, swappable batteries. One of the external, swappable batteries resides within the wristband, while the other external, swappable battery charges in the tablet by way of the tablet's onboard battery. The tablet functionality is contingent on both batteries being in place and the wristband battery having at least 50% charge. When the wristband's external battery drops below 50%, a notification is sent to the tablet and the wristband, indicating that the batteries need to be switched out to maintain normal tablet operations. If the battery level drops to 10%, a notification is sent to the staff to ensure compliance and avoid power loss. When the notification is sent to the wristband, the alert lights 410 illuminate in a particular manner that is different from when the battery is at or above 50% charge level. For example, a low battery notification (when the wristband battery charge is less than 50%) triggers the alert lights 410 to change from a green color to a red color, indicating that the battery is less than 50% charged.

As shown in FIG. 5, the bottom side of the wireless wristband device 500 demonstrates a health monitoring sensor system 510 with one or more sensors configured to detect health and vital signs of a custodial inpatient wearing the wireless wristband device.

While the wireless wristband device shown in FIGS. 4 and 5 demonstrate one exemplary design, the wristband device utilized in any health monitoring and location tracking behavior modification system deployment may have other designs and appearances, so long as the core functionality of the wristband device remains present, namely, that the wristband device confers a verifiable way to identify the custodial inpatient via unique ID, also providing a method to authenticate the custodial inpatient for access to the tablet features, to monitor and log the health and vital signs of the custodial inpatient, and to track and log location of the custodial inpatient by wireless pairing/connection to locator beacons spread in and around the facility.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 6:
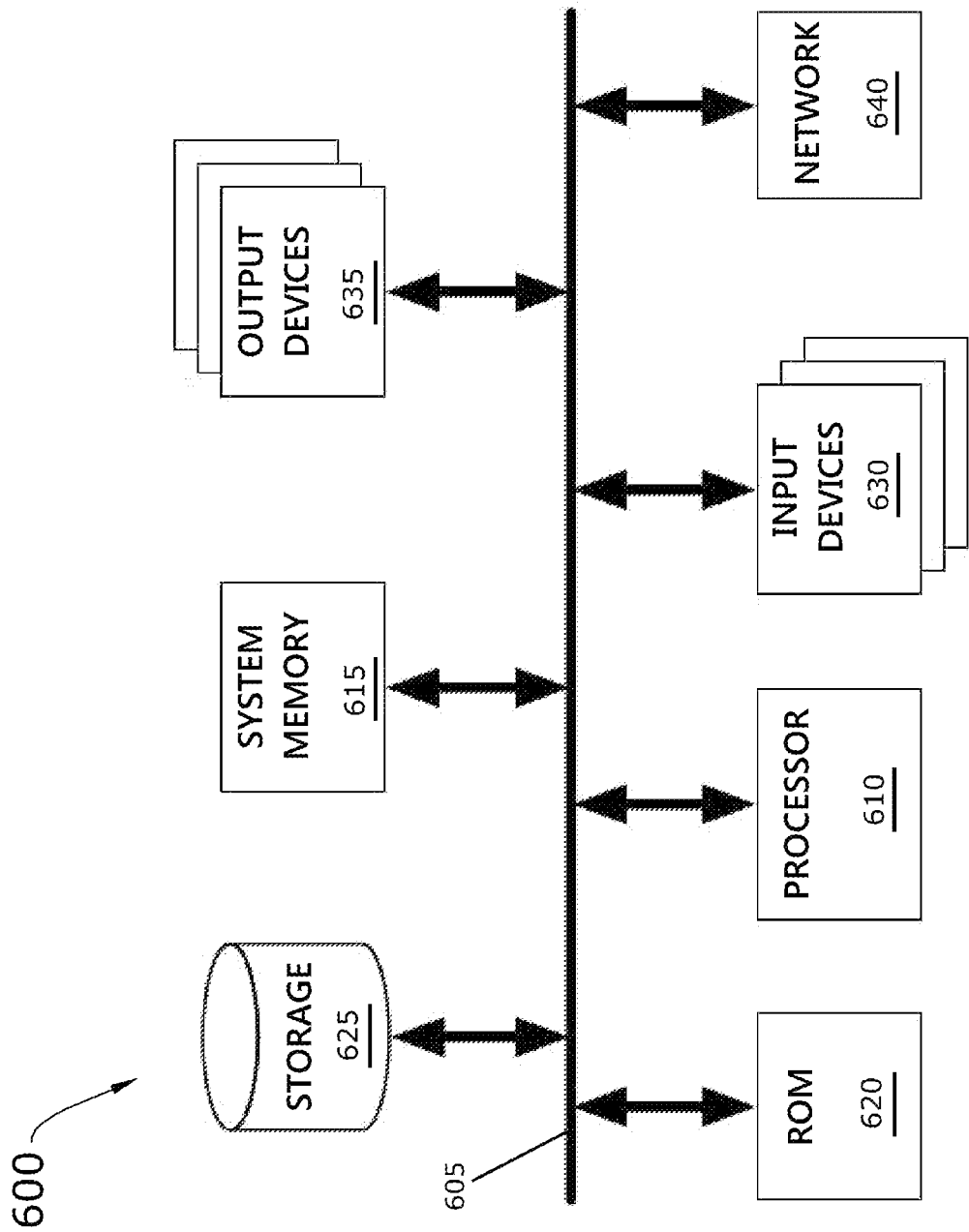
FIG. 6 conceptually illustrates an electronic system with which some embodiments of the invention are implemented.

FIG. 6 conceptually illustrates an electronic system 600 with which some embodiments of the invention are implemented. The electronic system 600 may be a tablet computing device or another mobile device suitable for use by incarcerated individuals on a token-based reward basis, or may be any other sort of electronic device that could be designed and used according to the various embodiments of the invention described above. Such an electronic system includes various types of computer readable media and interfaces for various other types of computer readable media. Electronic system 600 includes a bus 605, processing unit(s) 610, a system memory 615, a read-only memory 620, a permanent storage device 625, input devices 630, output devices 635, and a network 640.

The bus 605 collectively represents all system, peripheral, and chipset buses that communicatively connect the numerous internal devices of the electronic system 600. For instance, the bus 605 communicatively connects the processing unit(s) 610 with the read-only memory 620, the system memory 615, and the permanent storage device 625.

From these various memory units, the processing unit(s) 610 retrieves instructions to execute and data to process in order to execute the processes of the invention. The processing unit(s) may be a single processor or a multi-core processor in different embodiments.

The read-only-memory (ROM) 620 stores static data and instructions that are needed by the processing unit(s) 610 and other modules of the electronic system. The permanent storage device 625, on the other hand, is a read-and-write memory device. This device is a non-volatile memory unit that stores instructions and data even when the electronic system 600 is off. Some embodiments of the invention use a mass-storage device (such as a magnetic or optical disk and its corresponding disk drive) as the permanent storage device 625.

Other embodiments use a removable storage device (such as a floppy disk or a flash drive) as the permanent storage device 625. Like the permanent storage device 625, the system memory 615 is a read-and-write memory device. However, unlike storage device 625, the system memory 615 is a volatile read-and-write memory, such as a random access memory. The system memory 615 stores some of the instructions and data that the processor needs at runtime. In some embodiments, the invention's processes are stored in the system memory 615, the permanent storage device 625, and/or the read-only memory 620. From these various memory units, the processing unit(s) 610 retrieves instructions to execute and data to process in order to execute the processes of some embodiments.

The bus 605 also connects to the input and output devices 630 and 635. The input devices enable the user to communicate information and select commands to the electronic system. The input devices 630 include alphanumeric keyboards and pointing or cursor control devices. The output devices 635 include printers and display devices, such as liquid crystal displays (LCD) and organic light emitting diode (OLED) displays. Some embodiments include devices such as a touchscreen of the tablet computing device, which as a touch input device and a visual output device, functions as both input and output devices.

Finally, as shown in FIG. 6, bus 605 also couples electronic system 600 to a network 640 through a network adapter (not shown). In this manner, the computer can be a part of a network of computers (such as a local area network ("LAN"), a wide area network ("WAN"), or an Intranet), or a network of networks (such as the Internet). Any or all components of electronic system 600 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes and logic flows may be performed by one or more programmable processors and by sets of programmable logic circuitry. General and special purpose computing and storage devices can be interconnected through communication networks including, without limitation, a local wireless network (such as WiFi), a cellular network that supports cellular connectivity to a cell tower, or other wireless communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD−RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The above-described embodiments of the invention are presented for purposes of illustration and not of limitation. While the invention has been described with reference to numerous specific details, one of ordinary skill in the art will recognize that the invention can be embodied in other specific forms without departing from the spirit of the invention. For instance, FIGS. 2 and 3 conceptually illustrate processes. The specific operations of each process may not be performed in the exact order shown and described. Specific operations may not be performed in one continuous series of operations, and different specific operations may be performed in different embodiments. Furthermore, each process could be implemented using several sub-processes, or as part of a larger macro process. Thus, one of ordinary skill in the art would understand that the invention is not to be limited by the foregoing illustrative details, but rather is to be defined by the appended claims.

We claim:

1. A health monitoring and location tracking behavior modification system comprising:
   a wireless locator beacon device that provides location tracking of a custodial inpatient at a facility;
   a tablet computing device configured for operation by the custodial inpatient to engage in communication and interact with rehabilitative and entertainment content;
   a wearable wristband device that is worn by the custodial inpatient and is configured to perform realtime health monitoring of the custodial inpatient, verify identity of the custodial inpatient during operation of the tablet computing device, and track location of the custodial inpatient in realtime in connection with the wireless locator beacon; and
   a token-based reward system that is configured to provide an incentive for positive conduct by the custodial inpatient in the form of digital tokens for entertainment and recreational communication usage of the tablet computing device.

2. The health monitoring and location tracking behavior modification system of claim 1, wherein the wireless locator beacon device is a particular wireless locator beacon device placed in a particular holding cell assigned to the custodial inpatient.

3. The health monitoring and location tracking behavior modification system of claim 2 further comprising a plurality of wireless locator beacon devices placed at a plurality of locations in and around the facility.

4. The health monitoring and location tracking behavior modification system of claim 3, wherein the plurality of wireless locator beacon devices comprise the particular wireless locator beacon device placed in the particular holding cell assigned to the custodial inpatient and other holding cell wireless locator beacon devices placed in holding cells assigned to other custodial inpatients.

5. The health monitoring and location tracking behavior modification system of claim 1, wherein the wearable wristband device worn by custodial inpatient comprises a unique ID that is associated with the custodial inpatient and is used to verify identity of the custodial inpatient during operation of the tablet computing device.

6. The health monitoring and location tracking behavior modification system of claim 1, wherein the digital tokens provided by the token-based reward system comprise a standard allotment of digital tokens when positive conduct is demonstrated during an entire day by the custodial inpatient.

7. The health monitoring and location tracking behavior modification system of claim 6, wherein the standard allotment of digital tokens is distributed to the custodial inpatient at lockdown and are available to use during a following day by the custodial inpatient for entertainment and recreational communication usage of the tablet computing device.

8. The health monitoring and location tracking behavior modification system of claim 1, wherein the token-based reward system discourages negative conduct by the custodial inpatient by reducing entertainment and recreational communication usage of the tablet computing device.

9. The health monitoring and location tracking behavior modification system of claim 8, wherein legal and medical communication and health application usage of the tablet computing device remains available to use by the custodial inpatient irrespective of negative conduct of the custodial inpatient.

* * * * *